(12) United States Patent
Zhu

(10) Patent No.: US 9,638,611 B2
(45) Date of Patent: May 2, 2017

(54) SAMPLING UNIT FOR CONCENTRATES PREPARATION DEVICE

(71) Applicant: Gong Zhu, Xiamen (CN)

(72) Inventor: Gong Zhu, Xiamen (CN)

( * ) Notice: Subject to any disclaimer, the term of this patent is extended or adjusted under 35 U.S.C. 154(b) by 42 days.

(21) Appl. No.: 14/953,298

(22) Filed: Nov. 27, 2015

(65) Prior Publication Data

US 2016/0153879 A1 Jun. 2, 2016

(30) Foreign Application Priority Data

Nov. 28, 2014 (CN) .......................... 2014 1 0706732

(51) Int. Cl.
*G01N 1/02* (2006.01)
*G01N 1/00* (2006.01)
*G01N 1/40* (2006.01)

(52) U.S. Cl.
CPC ... *G01N 1/4022* (2013.01); *G01N 2001/4033* (2013.01)

(58) Field of Classification Search
CPC ........... G01N 1/00; G01N 1/02; G01N 1/4022
USPC ...................................... 73/862.12
See application file for complete search history.

(56) References Cited

U.S. PATENT DOCUMENTS

| | | | | |
|---|---|---|---|---|
| 4,594,904 A | * | 6/1986 | Richter | ...................... C10J 3/22 73/863.11 |
| 5,567,888 A | * | 10/1996 | Boydle | ..................... G01N 1/10 73/863.86 |
| 2007/0074761 A1 | * | 4/2007 | Salomon | ................. F16K 1/446 137/240 |
| 2008/0307901 A1 | * | 12/2008 | Knight | ................. G01N 1/2247 73/863.11 |
| 2013/0125673 A1 | * | 5/2013 | Kanipayor | ................ B01L 3/04 73/863.11 |

FOREIGN PATENT DOCUMENTS

| | | | | |
|---|---|---|---|---|
| CA | WO 2011054086 A1 | * | 5/2011 | ............... B01L 3/04 |
| CN | 201251521 Y | * | 6/2009 | |
| CN | 204293896 U | | 4/2015 | |
| FR | EP 0455333 A2 | * | 11/1991 | ............. B01D 35/26 |

* cited by examiner

*Primary Examiner* — Lisa Caputo
*Assistant Examiner* — Jamel Williams

(57) ABSTRACT

The invention relates to a sampling unit for the concentrates preparation device. The unit comprises a base body, a movable rod, a limiting pin, a sampling chamber, a sampling bore, an axle sleeve and an isobaric chamber. The sampling chamber passes through the upper and lower surfaces of the base body, the isobaric chamber is a cylindrical blind bore, the isobaric chamber passes through the front surface of the base body and passes through the front and back surfaces of the sampling chamber. The axle sleeve has an interference fitting with the isobaric chamber, the movable rod hermetically slidingly mates with the axle sleeve, the head and tail ends of the gas permeable passage respectively communicate with the isobaric chamber and the outside. Concentrates can be taken out through the sampling bore of the sampling unit, the movable rod can take samples freely with the help of gas permeable passage for keeping the pressure balance of ends of the movable rod.

4 Claims, 6 Drawing Sheets

SAMPLING UNIT FOR CONCENTRATES PREPARATION DEVICE

FIELD OF THE INVENTION

The invention relates to a concentrates preparation device, especially to a sampling unit for the concentrates preparation device using low pressure and low boiling point.

DESCRIPTION OF PRIOR ART

The boiling point of water decreases with the pressure, so water can be boiling with low temperature under low pressure, the boiling water changes liquid water into water vapor, mist water vapor condenses on the interface between cool and hot, a lot of mist collects together to form water drop, and a lot of water drop collects together to form water flow, whether we can use the above principle to lower the moisture content of the mixture so as to increase the concentration.

So, there is provided with a device which can remove water from mixture using above principle, the device is a concentrates preparation device, which condenses hot water steam into liquid water, which is transformed to the container latter, thereby water content is reduced, so the concentrating function is achieved.

It is a problem to take samples of the concentrates in the boiler when it is need to detect the density of the concentrates in the boiler.

SUMMARY OF THE PRESENT INVENTION

The object of the invention is to provide a sampling unit for the concentrates preparation device so as to solve the above problem.

Therefore, the invention provide a sampling unit for the concentrates preparation device, the sampling unit comprises
a base body; the sampling unit further includes a movable rod, a limiting pin, a sampling chamber, a sampling bore, an axle sleeve and an isobaric chamber. The sampling chamber passes through the upper and lower surfaces of the base body; the isobaric chamber is configured to be a cylindrical blind bore, the isobaric chamber passes through the front surface of the base body and passes through the front and back surfaces of the sampling chamber. The axle sleeve has an interference fitting with the isobaric chamber, the movable rod hermetically slidingly mates with the axle sleeve, the limiting pin fastened on the movable rod mates with the front surface or the back surface of the sampling chamber, inside the base body is provided with a gas permeable passage, of which the head and tail ends respectively communicate with the isobaric chamber and the outside.

Profitably, the movable rod is at the withdraw position and the sampling bore is outside the base body when the limiting pin mates with the front surface of the sampling chamber; the movable rod is at the insertion position and the sampling bore is inside the sampling chamber when the limiting pin mates with the back surface of the sampling chamber.

Profitably, the gas permeable passage extends to the front surface of the base body, the sampling chamber of the sampling unit is inside the boiler, the handle is outside the boiler.

Profitably, the sampling unit is arranged near to the bottom portion of the sidewall of the boiler unit.

Advantageous Effects

When the sampling unit takes samples of concentrates from the boiler, it is no necessary to stop concentration process or to open the upper cover of the boiler. Concentrates in the boiler can be taken out through the sampling bore of the sampling unit, the movable rod can take samples freely with the help of gas permeable passage for keeping the pressure balance of ends of the movable rod.

BRIEF DESCRIPTION OF THE DRAWING

In the following, the invention will be described in greater detail by means of some embodiments with reference to the accompanying drawings, in which.

DETAILED DESCRIPTION OF THE PREFERRED EMBODIMENT

Figure 1:
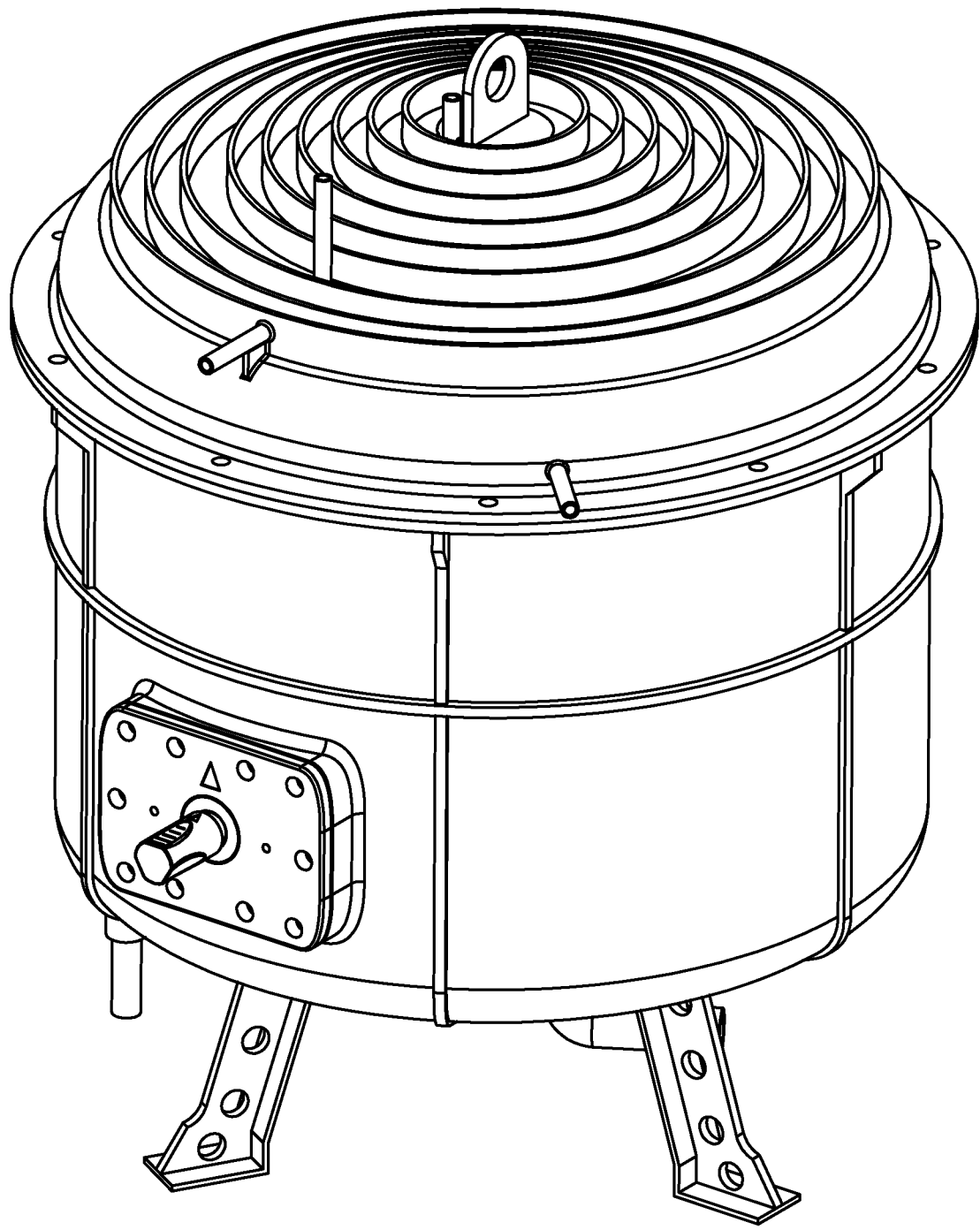
FIG. 1 is a 3d-drawing of the boiler.
Figure 7:
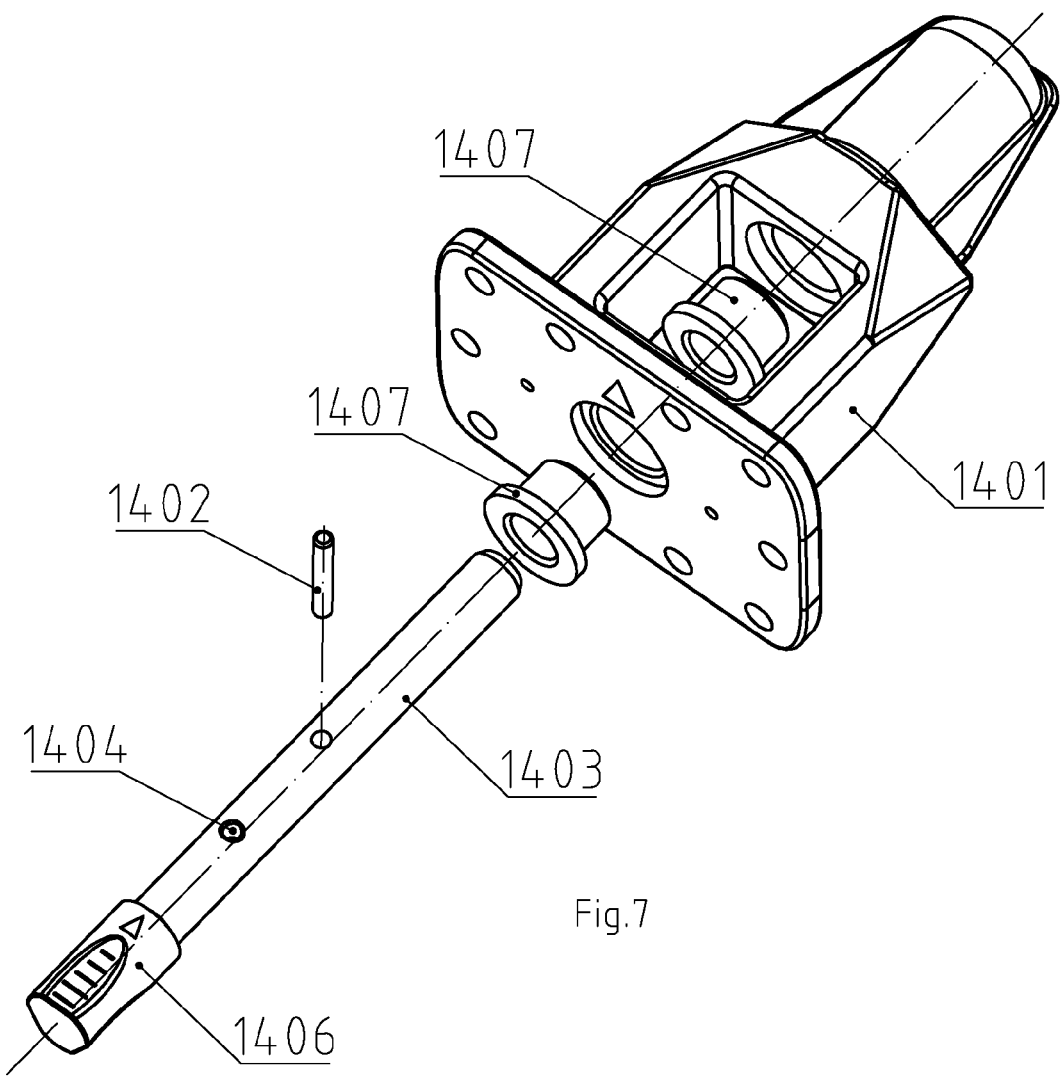
FIG. 7 is an exploded 3d-drawing of the sampling unit.

Referring to FIG. 1, it is a boiler unit suitable for the concentrates preparation device of the invention. A sampling unit 14 is arranged near to the bottom portion of the sidewall of the boiler unit, referring to FIG. 7 and FIG. 8, the sampling unit 14 is provided with a movable rod 1403, a limiting pin 1402, a sampling chamber 1405, a sampling bore 1404, an axle sleeve 1407 and an isobaric chamber 1409.

Figure 9:
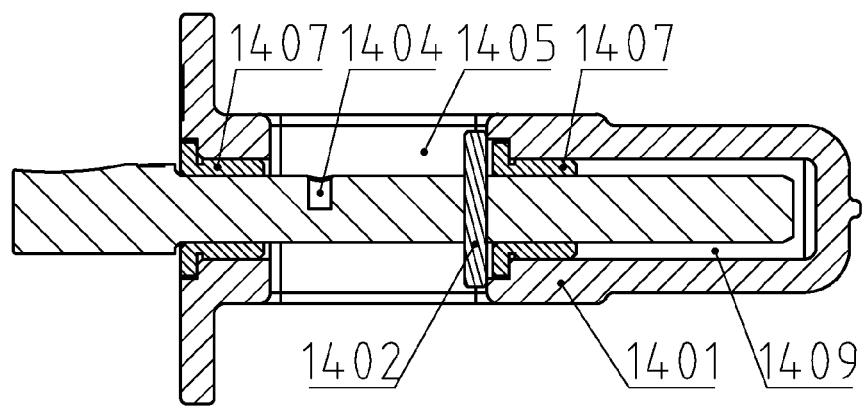
FIG. 9-11 are sectional front drawings of the sampling unit, wherein the movable rod is at different positions.
14. the sampling unit; 1401. the base body;
1402. the limiting pin; 1403. the movable rod;
1404. the sampling bore; 1405. the sampling chamber;
1406. the handle; 1407. the shaft sleeve;
1408. the gas permeable passage; 1409. the isobaric chamber.

Referring to FIG. 9, the sampling chamber 1405 passes through the upper and lower surfaces of the base body 1401, the isobaric chamber 1409 is configured to be a cylindrical blind bore, the isobaric chamber 1409 passes through the front surface of the base body 1401 and passes through the front and back surfaces of the sampling chamber 1405. The axle sleeve 1407 has an interference fitting with the isobaric chamber 1409, the movable rod 1403 hermetically slidingly mates with the axle sleeve 1407, the limiting pin 1402 is fastened on the movable rod 1403.

Figure 2:
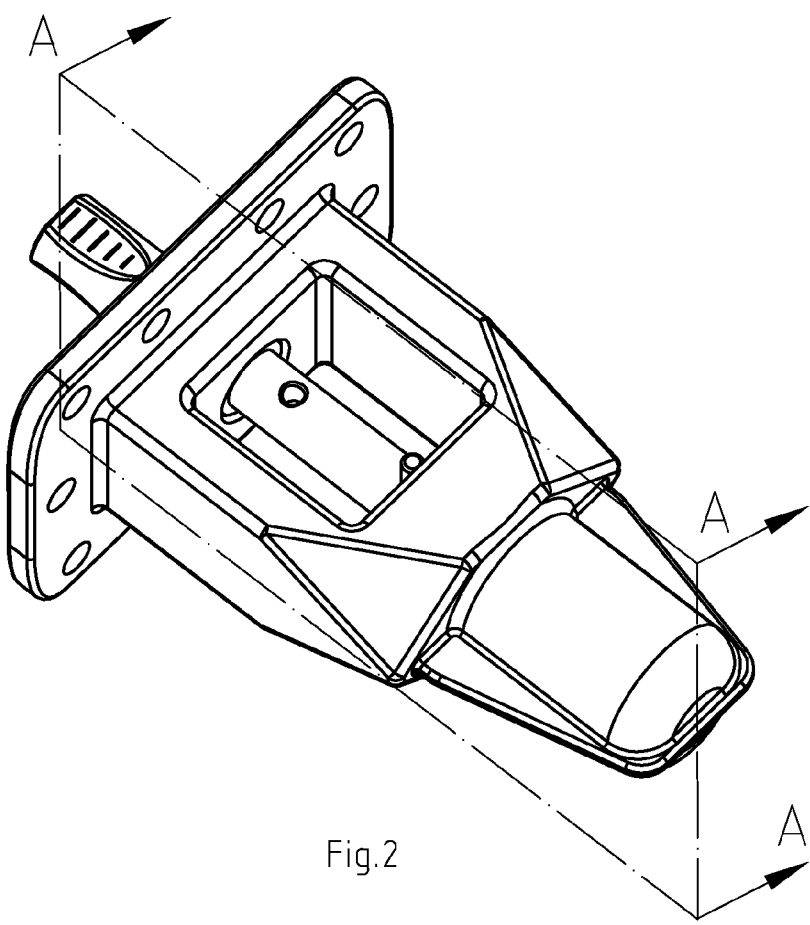
FIG. 2-6 are 3d-drawings of the sampling unit, wherein the movable rod is at different positions.
Figure 3:
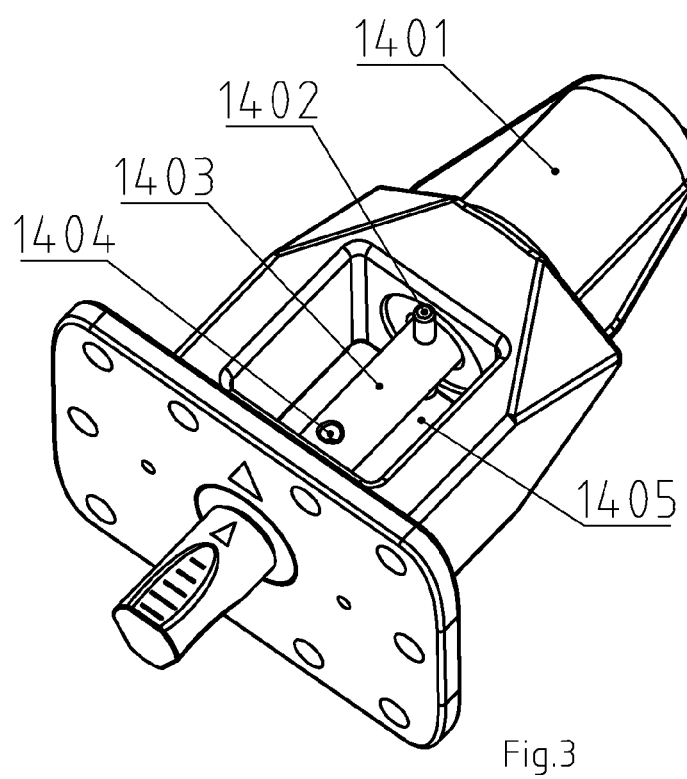
Figure 4:
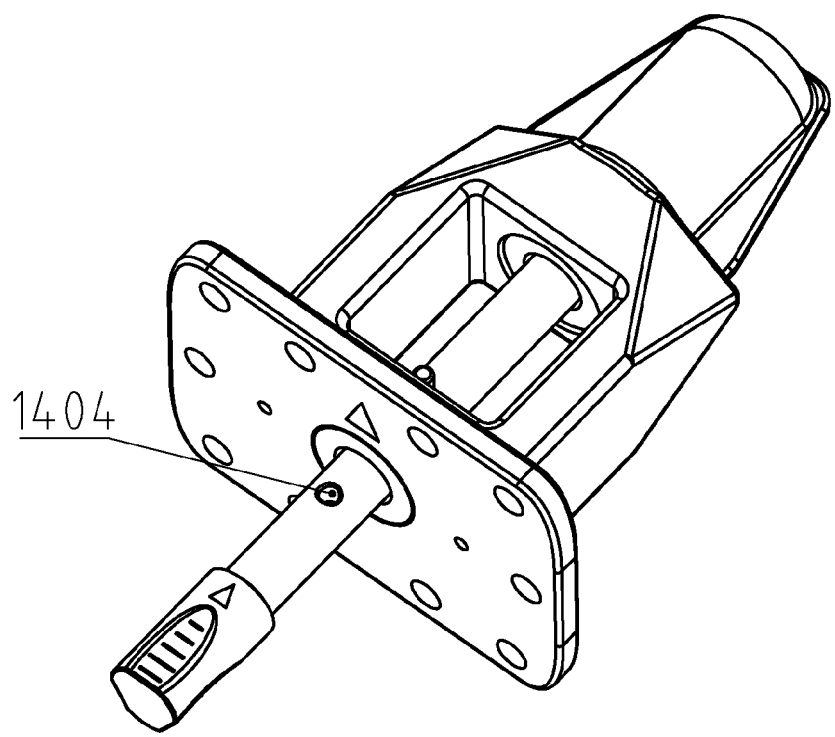
Figure 5:
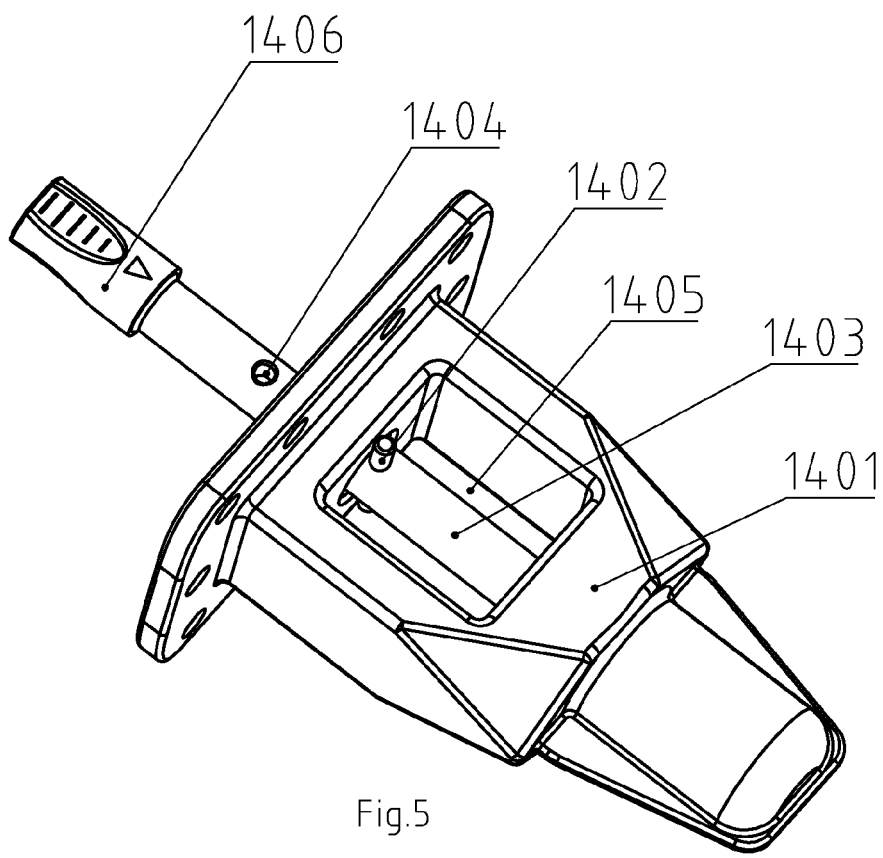
Figure 6:
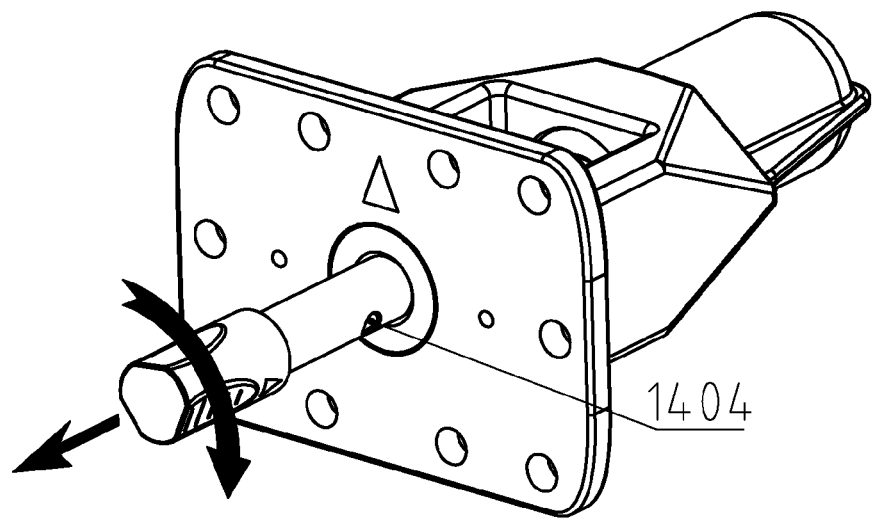
Figure 10:
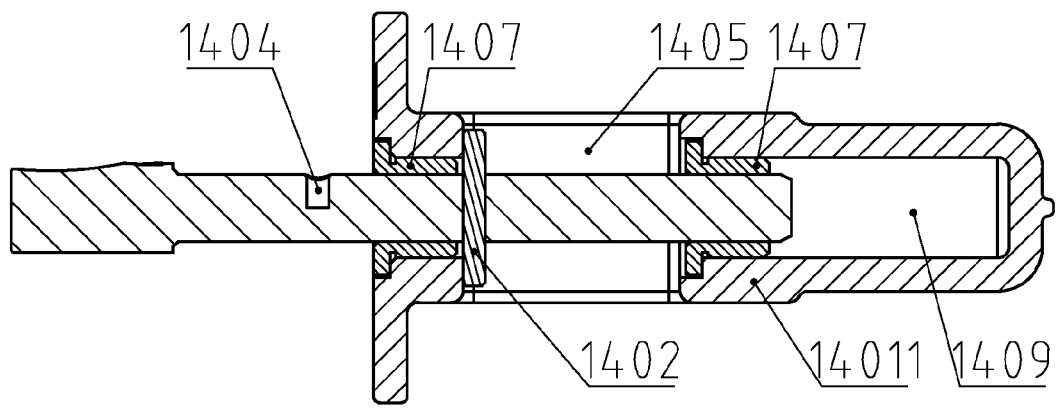
Figure 11:
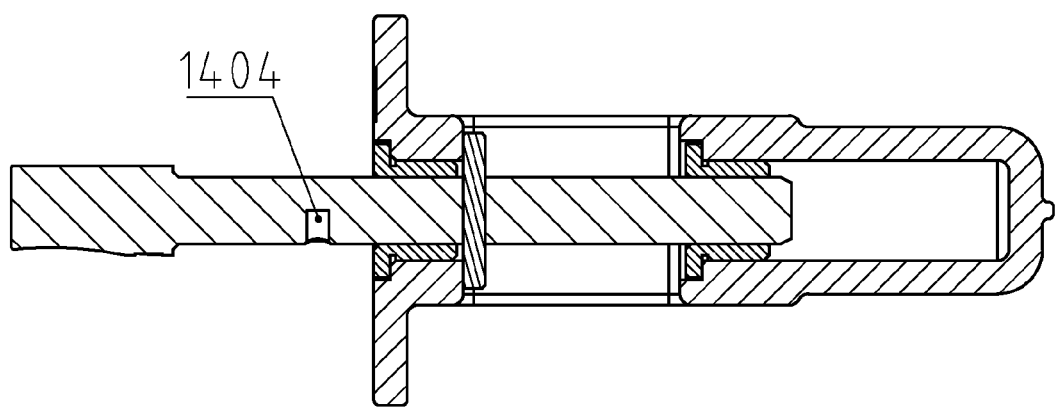

Referring to FIG. 9 and FIG. 10, the movable rod 1403 is at the withdraw position and the sampling bore 1404 is outside the base body 1401 when the limiting pin 1402 mates with the front surface of the sampling chamber 1405, referring to FIG. 4 and FIG. 5. The movable rod 1403 is at the insertion position and the sampling bore 1404 is inside the sampling chamber 1405 when the limiting pin 1402 mates with the back surface of the sampling chamber 1405, referring to FIG. 2 and FIG. 3.

Figure 8:
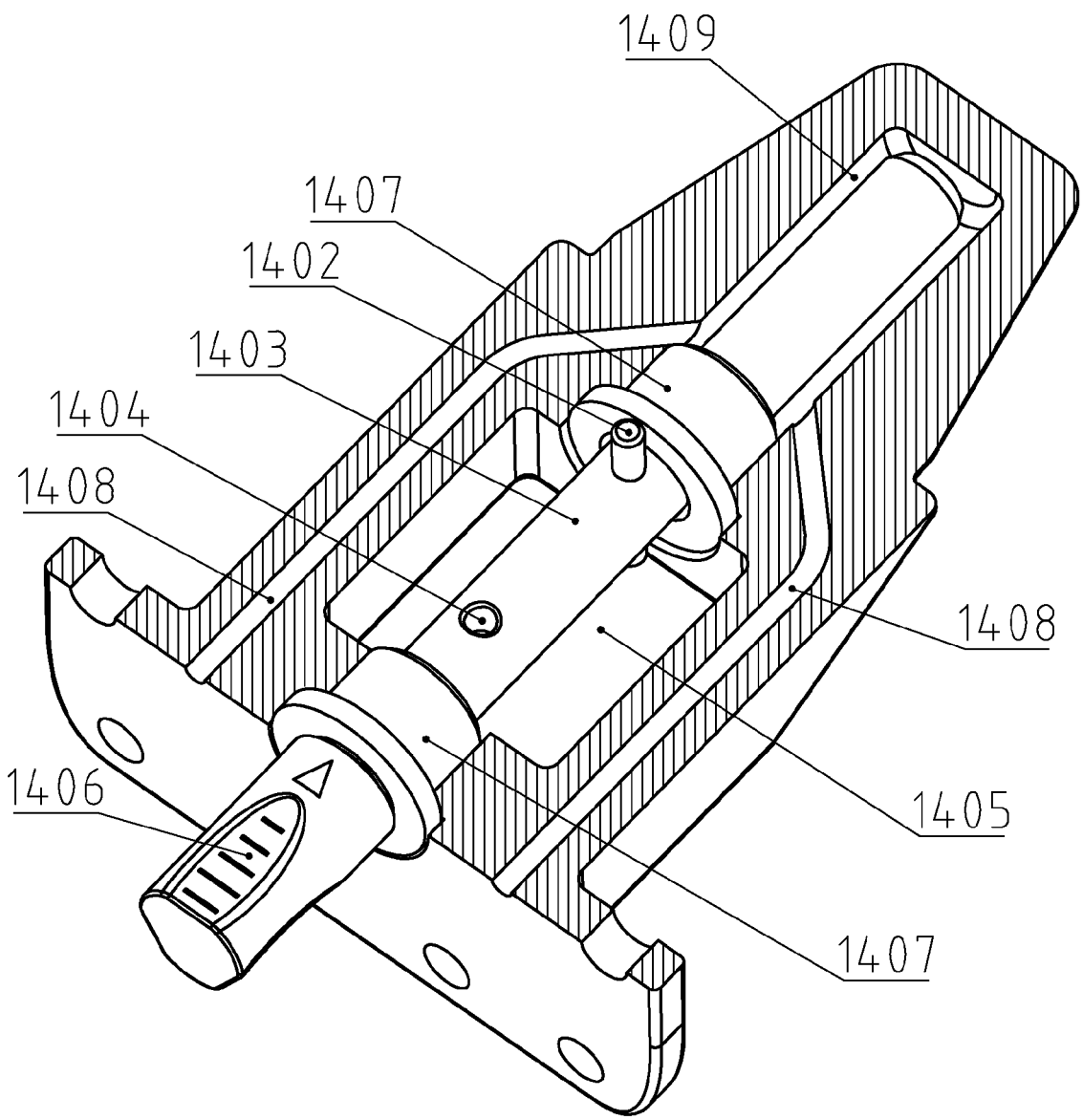
FIG. 8 is a sectional 3d-drawing of the sampling unit.

Referring to FIG. 8, inside the base body 1401 is provided with a gas permeable passage 1408, of which the head and tail ends respectively communicate with the isobaric chamber 1409 and the outside atmosphere, the air permeable passage 1408 extends to the front surface of the base body

1401, air pressure of the isobaric chamber 1409 is equal to the outside air pressure with the help of the gas permeable passage 1408 so as to make the movable rod 1403 moves more flexibly. The movable rod 1403 near to the front surface of the base body 1401 is provided with a handle 1406, of which the diameter is greater than the interior diameter of the shaft sleeve 1407, the sampling chamber 1405 of the sampling unit 14 is inside the boiler, the handle 1406 is outside the boiler.

Referring to FIG. 9,10,11, the sampling unit 14 takes samples of concentrates in the boiler during the concentrating process to make concentration detection of samples. In order to increase detecting accuracy, the handle 1406 is rotated fast before sampling, referring to FIG. 18, the remnant sample left in the sampling bore 1404 is thrown out due to the centrifugal force, then the sampling bore is upwards with the help of the direction mark on the handle 1406; the movable rod 1403 is drawn out to the withdraw position after the sampling bore 1404 is full of concentrates, detector detects the concentration of the sample in the sampling bore, or detector detects the concentration of the sample in the glassware dropped from the sampling bore due to the gravity force after rotating the movable rod 1403 to make the sampling bore 1404 be downwards. The movable rod 1403 is pushed back to the insertion position after sampling process.

The base body 1401 of the sampling unit 14 can be achieved by investment casting process, the cylindrical isobaric chamber can be manufactured by secondary processing like boring for an interference fitting with axle sleeve 1407.

The invention claimed is:

1. A sampling unit for the concentrates preparation device, comprising a base body (1401); characterized in that
the sampling unit (14) is provided with a movable rod (1403), a limiting pin (1402), a sampling chamber (1405), a sampling bore (1404), an axle sleeve (1407) and an isobaric chamber (1409); the sampling chamber (1405) passing through the upper and lower surfaces of the base body (1401), the isobaric chamber (1409) being a cylindrical blind bore, the isobaric chamber (1409) passing through the front surface of the base body (1401) and passing through the front and back surfaces of the sampling chamber (1405);
the axle sleeve (1407) having an interference fitting with the isobaric chamber (1409), the movable rod (1403) hermetically slidingly matting with the axle sleeve (1407), the limiting pin (1402) fastened on the movable rod (1403), the limiting pin (1402) matting with the front surface or the back surface of the sampling chamber (1405), inside the base body (1401) provided with a gas permeable passage (1408), of which the head and tail ends respectively communicating with the isobaric chamber (1409) and the outside.

2. A sampling unit for the concentrates preparation device according to claim 1, characterized in that
the movable rod (1403) is at the withdraw position and the sampling bore (1404) is outside the base body (1401) when the limiting pin (1402) mates with the front surface of the sampling chamber (1405); the movable rod (1403) being at the insertion position and the sampling bore (1404) being inside the sampling chamber (1405) when the limiting pin (1402) mates with the back surface of the sampling chamber (1405).

3. A sampling unit for the concentrates preparation device according to claim 1, characterized in that
the gas permeable passage (1408) extends to the front surface of the base body (1401), the sampling chamber (1405) of the sampling unit (14) being inside the boiler, the handle (1406) being outside the boiler.

4. A sampling unit for the concentrates preparation device according to claim 1, characterized in that
the sampling unit (14) is arranged near to the bottom portion of the sidewall of the boiler unit.

* * * * *